(12) United States Patent
Li et al.

(10) Patent No.: US 9,037,270 B2
(45) Date of Patent: May 19, 2015

(54) ELECTRONIC STIMULATION TEXTILE FOR TRADITIONAL CHINESE MEDICINE THERAPY

(75) Inventors: Li Li, Hong Kong (HK); Wai Man Raymond Au, Hong Kong (HK); Kwok Shing Thomas Wong, Hong Kong (HK); Wai Yee Joanne Chung, Hong Kong (HK); Kam Man Wan, Hong Kong (HK); Sai Ho Wan, Hong Kong (HK)

(73) Assignee: The Hong Kong Polytechnic University, Hung Hom, Kowloon (HK)

( * ) Notice: Subject to any disclaimer, the term of this patent is extended or adjusted under 35 U.S.C. 154(b) by 274 days.

(21) Appl. No.: 12/569,893

(22) Filed: Sep. 29, 2009

(65) Prior Publication Data

US 2011/0077728 A1   Mar. 31, 2011

(51) Int. Cl.
*A61N 1/04* (2006.01)
*A61N 1/36* (2006.01)
*A61H 39/00* (2006.01)

(52) U.S. Cl.
CPC ........ *A61N 1/36021* (2013.01); *A41D 2400/32* (2013.01); *A61H 39/002* (2013.01); *A61H 2201/165* (2013.01); *A61N 1/0456* (2013.01); *A61N 1/0484* (2013.01)

(58) Field of Classification Search
CPC ............ A61N 1/36021; A61N 1/0456; A61N 1/0484; A61H 32/002
USPC .......................... 128/907; 607/148, 150, 142
See application file for complete search history.

(56) References Cited

U.S. PATENT DOCUMENTS

| 4,580,572 | A | * | 4/1986 | Granek et al. ................. 600/388 |
| 6,728,577 | B2 | * | 4/2004 | Minogue et al. ................. 607/48 |
| 7,877,152 | B2 | * | 1/2011 | Chu ............................... 607/145 |
| 2005/0055054 | A1 | * | 3/2005 | Yu ..................................... 607/2 |
| 2005/0055066 | A1 | * | 3/2005 | Yu ................................... 607/48 |
| 2006/0030879 | A1 | | 2/2006 | Spector | |

* cited by examiner

*Primary Examiner* — Amanda Patton
(74) *Attorney, Agent, or Firm* — The Hong Kong Polytechnic University

(57) ABSTRACT

A textile for providing traditional Chinese medicine therapy to a wearer using electronic stimulation includes at least two conductive paths that are made from conductive textile material, the conductive paths are separated by nonconductive textile material, at least one pair of electrodes attach to the conductive paths corresponding to specific part of body or acupoints according to traditional Chinese medicine theory, and an electronic stimulation signal controller configured to conduct electronic stimulation signals to the electrodes via the conductive paths.

11 Claims, 5 Drawing Sheets

Back

Front

ELECTRONIC STIMULATION TEXTILE FOR TRADITIONAL CHINESE MEDICINE THERAPY

BACKGROUND OF THE INVENTION

1. Field of the Invention

The present invention is related to textiles with electronic stimulation function on specific body parts, more particular, the present invention relates to textiles that performs electronic stimulation for traditional Chinese medicine therapy.

2. Description of the Related Art

In the treatment of various types of diseases, pains, and disorders of the body, it is often advantageous to apply neurostimulation, such as electronic stimulation to the afflicted area, or more desirable still, to stimulate the nervous system, etc. Electronic stimulation may be performed by placing a pair of electrodes on the specific body area and conduct electrical pulses into the surrounding tissue. The electrode, or a plurality of electrodes, may be placed near a certain location on the spine or other area to suppress the pain. Stimulation may help to relieve pain by modulating nerve impulses to the brain that signal pain.

According to traditional Chinese medicine theory, puncturing the body with needles at acupuncture points (acupoints) can relieve pain and achieve various medical benefits. In acupuncture, health is maintained by the flow of Qi (life energy) through pathways of our bodies called meridians lines.

U.S. Pub. Appl. No. 2006/0030879 discloses an article of clothing that provides acupressure to acupoints. The wearer can perform acupressure on him or herself by pressing on the pellet, which applies pressure to the specific acupoint. The pellets are secured on specific area with an adhesive tape. However, the pellet does not provide electronic stimulation to the acupoints. Thus, the medical effects of this article of clothing are greatly limited. Electronic stimulation is an effective treatment for various diseases. Many studies have demonstrated the effectiveness of electronic stimulation if patient can use them continuously in the right way. In addition, various studies have demonstrated the results that patients in the electronic stimulation with acupuncture point stimulation had a better effect.

Furthermore, most of the conventional electrodes are made of silica gel hydro pads that can be adhered to human skin, which can be repeatedly used for a number of times. While the performance of this kind of electrode is good, the conventional electrodes are not suitable for textiles, for instance, the conventional electrodes are not washable and can cause discomfort to its wearer due to its stickiness etc.

There exists a potential application for wearable electronic textiles that provides electronic stimulation to the body with traditional Chinese medicine therapy for long-term continuous treatment.

SUMMARY OF THE INVENTION

According to an aspect of the present invention, a textile for providing traditional Chinese medicine therapy to a wearer using electronic stimulation includes at least two conductive paths that are made from conductive textile material, the conductive paths are separated by nonconductive textile material, at least one pair of electrodes attach to the conductive paths corresponding to specific part of body or acupoints according to traditional Chinese medicine theory, and an electronic stimulation signal controller configured to conduct electronic stimulation signals to the electrodes via the conductive paths.

Further features and aspects of the present invention will become apparent from the following description of exemplary embodiments with reference to the attached drawings.

DESCRIPTION OF THE EMBODIMENTS

The accompanying drawings, which are incorporated in and constitute a part of the specification, illustrate embodiments of the invention and, together with the description, serve to explain the principles of the invention.

The present invention is capable of providing acupuncture treatments to the wearer through strategically positioned electrodes at predetermined acupoints of a wearer.

Transcutaneous Electrical Nerve Stimulation (TENS) involves the passage of electrical current to electrodes passed on the skin. The current is delivered from a small battery-powered power unit. The time duration, frequency and intensity, etc, of this treatment depend on the specific condition and treatment goals. Accordingly, electrode pads may be placed in various specific positions on the body. TENS is a method to provide acupuncture treatment to a patient noninvasively. In TENS therapeutic method, current is applied to specific body area or acupoints by placing electrodes at the corresponding locations.

Electronic stimulation, such as TENS and Electrical Muscle Stimulation (EMS), etc, is widely used in the pain treatment or various types of diseases. Studies have shown that electronic stimulation demonstrated effectiveness on various diseases conditions if a patient uses it properly and continuously. Hence, it is desirable to provide electronic stimulation to a user in the form of a garment.

Figure 1A:
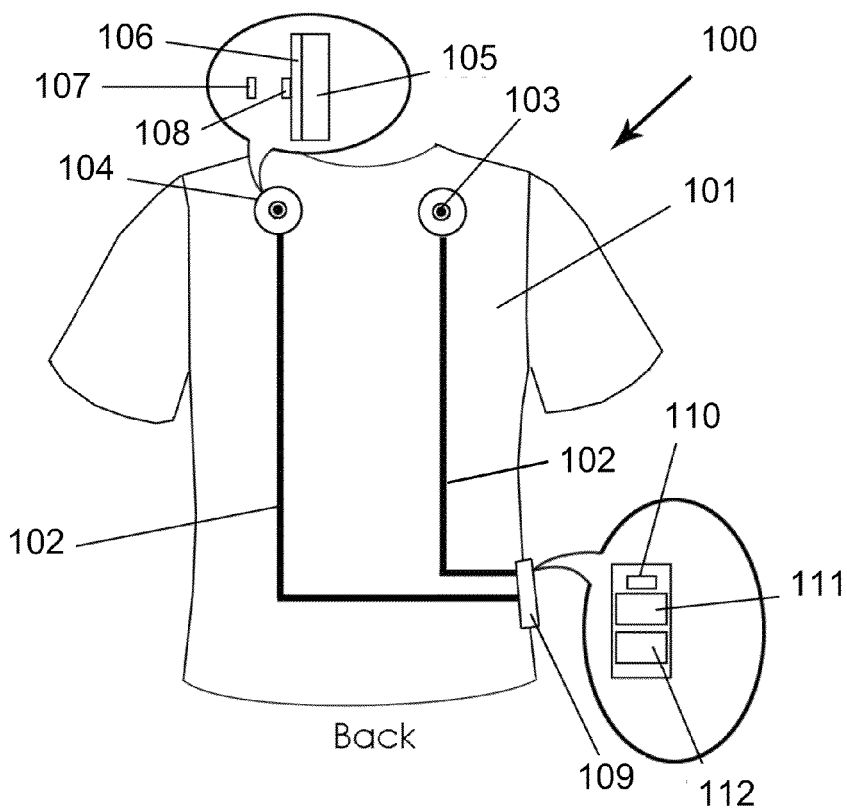
FIGS. 1A and 1B illustrate a back and front view of a garment according to an embodiment of the present invention.
Figure 1B:
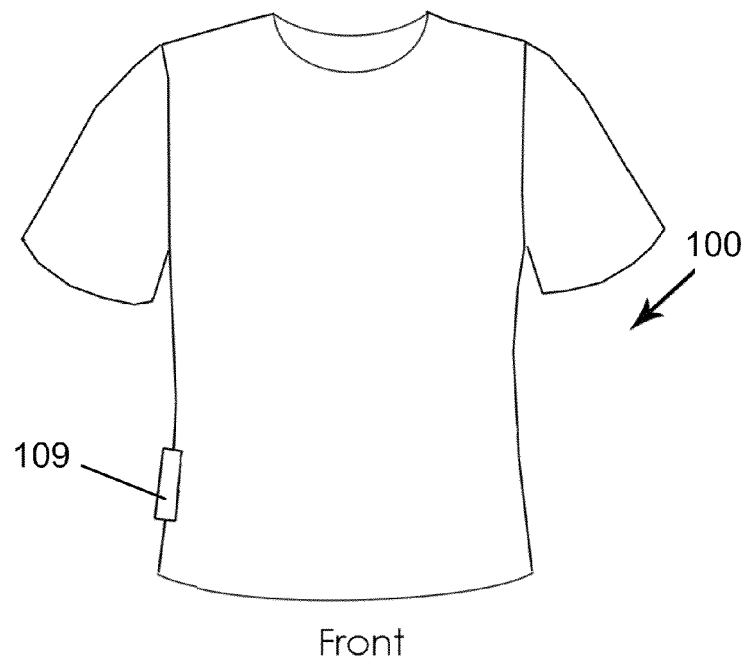

FIGS. 1A and 1B illustrate a back and front view of a garment 100, respectively, according to an embodiment of the present invention. The garment may include 2N electrodes, where N is a natural number. Conductive materials, such as silver conductive yarn, is knitted on the garment to serve as the electricity conducting wires as conductive paths 102.

Electrodes 103 and 104 are strategically positioned on the garment corresponding to the specific acupoints of a body part. The conductive paths 102 are separated by fabric 101 of garment 100, which is made of non-conductive material such as cotton or other non-conductive materials. The conductive material and the non-conductive material may also be connected by textiles technologies such as knitting, weaving, attaching, embroidering, sewing, printing and the like. The conductive paths 102 are connected to electrodes 103, 104 and electronic stimulation signal controller 109.

The electronic stimulation signal controller 109 may be placed inside a pocket, pouch, or the likes (not shown), of the garment 100. The electronic stimulation signal controller 109 contains at least two terminals that connect with the conductive paths 102 of the garment 100. The power source of the electronic stimulation signal controller 109 includes direct current, alternating current, batteries, renewable power, or the like. Stimulation frequency, intensity, pulse duration, arbitrary waveform pattern, treatment time, etc, can be preset and/or adjusted at the electronic stimulation signal controller 109. The electronic stimulation signal controller 109 includes a power button 110, battery 111, and control program 112. Battery 111 serves as a power source of electronic stimulation signal controller 109. Control program 112 includes computer executable program code that is stored inside a memory unit of the electronic stimulation signal controller 109 for controlling information such as stimulation frequency, intensity, pulse duration, waveform pattern, and treatment time, etc.

In this embodiment, by utilizing conductive paths that are made from conductive textiles, no electric wires are needed to connect with electronic stimulation signal controller with the electrodes. Electrodes 103 and 104 are made from conductive textile material, which are detachable from the garment 100. The top portion of electrode 104 is made from water absorbent material 105 (e.g., sponge-like material) so that the electrode may be moistened to increase its electrical conductivity. A layer of conductive material 106 (e.g., conductive fabric) is coated on bottom of the water absorbent material 105. A conductive connector on the electrode side 108 is attached on the layer of conductive material 106. A conductive connector on the electrode side 108 can be attached with conductive connector 107 on the garment side. Electrodes 103 and 104 can be attached on the garment 100 via an attachment means, such as conductive Velcro or a metallic dual-lock button, etc.

Figure 2A:
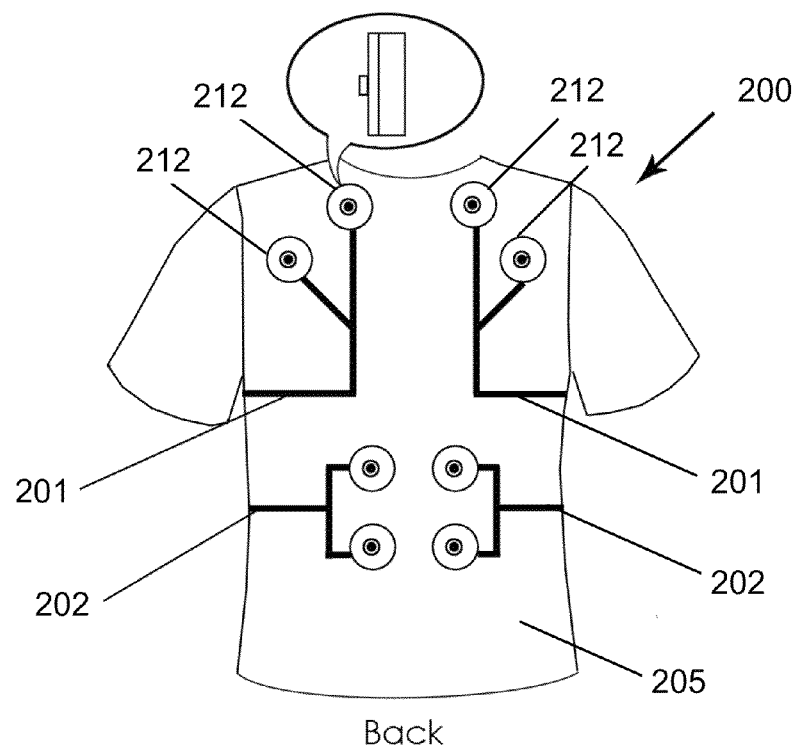
FIGS. 2A and 2B illustrate a back and front view of a garment according to another embodiment of the present invention.
Figure 2B:
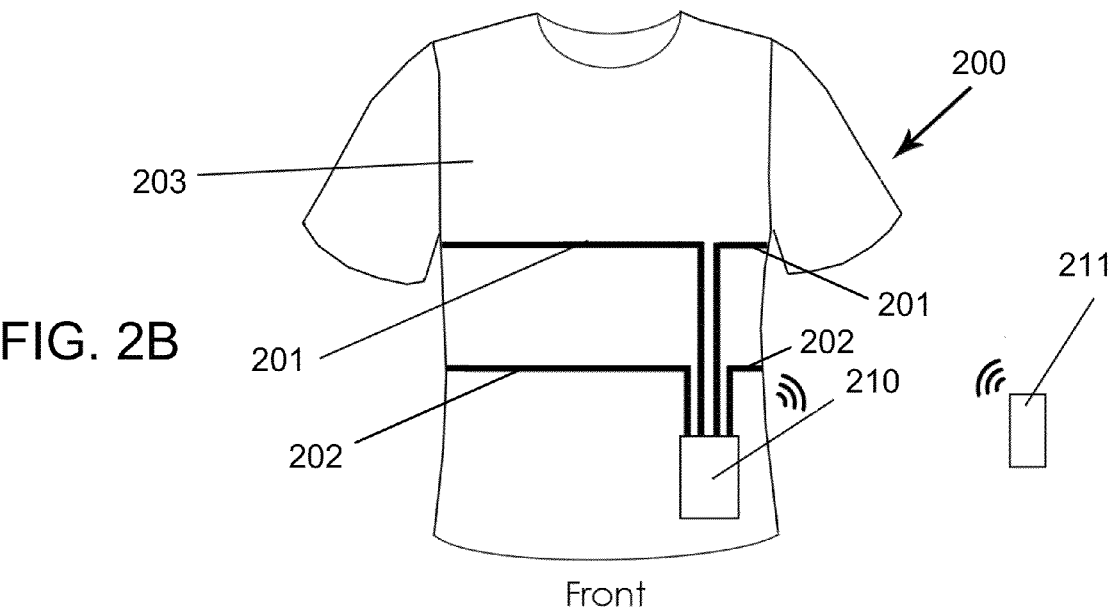

FIGS. 2A and 2B illustrate a back and front view of a garment 200, respectively, according to another embodiment of the present invention. The garment is made from nonconductive material 205. In this embodiment, each pair of conductive path (201 and 202) controls multiple electrodes.

The electrodes as shown in FIGS. 2A and 2B are the same as the electrodes described above in connection with FIGS. 1A and 1B. Thus, the descriptions thereof are omitted.

Both conductive paths 201 and 202 are connected to an electronic stimulation signal controller 210. In this embodiment, electronic stimulation signal controller 210 is wirelessly controlled by a remote device 211 via Bluetooth or the like. Thus, the controller 210 may includes a switch for selectively activate upper conductive path 201 or lower conductive path 202, or simultaneously activating both conductive paths 201 and 202. Stimulation frequency, intensity, pulse duration, waveform pattern, treatment time, etc, can be controlled at the remote device 211, or controlled by an embedded system of an electronic stimulation signal controller 210.

Figure 3A:
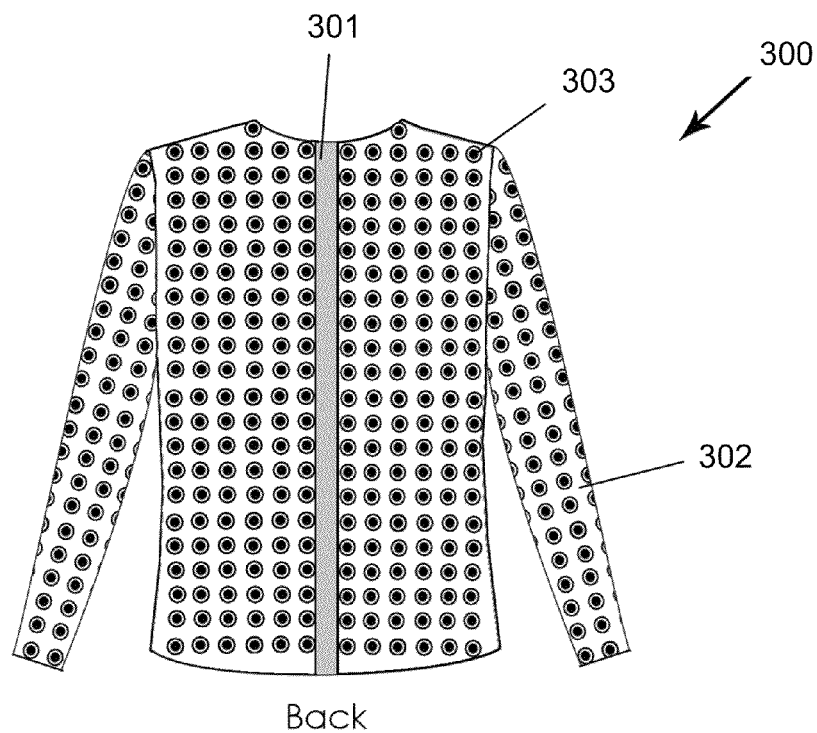
FIGS. 3A and 3B illustrate a back and front view of a garment according to another embodiment of the present invention.
Figure 3B:
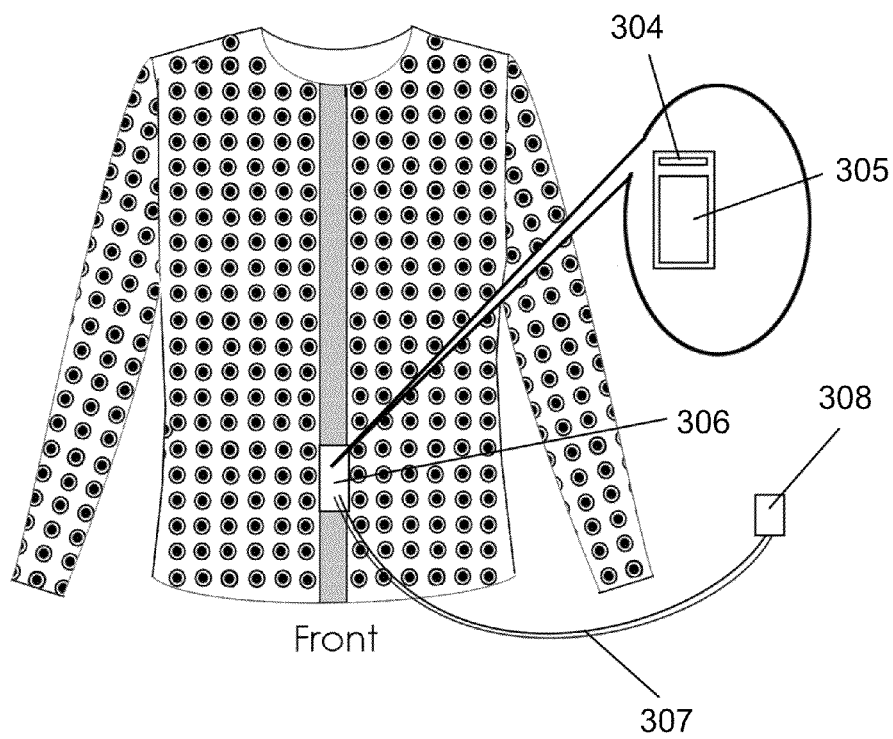

FIGS. 3A and 3B illustrates a back and front view of a garment 300, respectively, in accordance with another embodiment of the present invention. Fabric 301 is made from a nonconductive material, which is use for insulation of conductive paths in the garment 300. The other parts of the garment are made from conductive material 302, where the plurality of connectors (for connect electrode) 303 are installed throughout the conductive material 302 and the wearer of garment 300 can set which area to connect electrode 303 throughout the conductive material 302. Thus, the wearer can choose which area to activate the electrodes 303 by attaching the electrodes at the corresponding connectors. Stimulation frequency, intensity, pulse duration, waveform pattern, treatment time, etc, can be controlled at the electronic stimulation controller 306. The electronic stimulation signal controller 306 is connected with a power source 308 via an electrical wire 307. The signal controller includes a power button 304 and a control program 305 for controlling the electronic stimulation signal.

The electrodes as shown in FIGS. 3A and 3B are the same as the electrodes described above in connection with FIGS. 1A and 1B. Thus, the descriptions thereof are omitted.

Figures 4A, 4B:
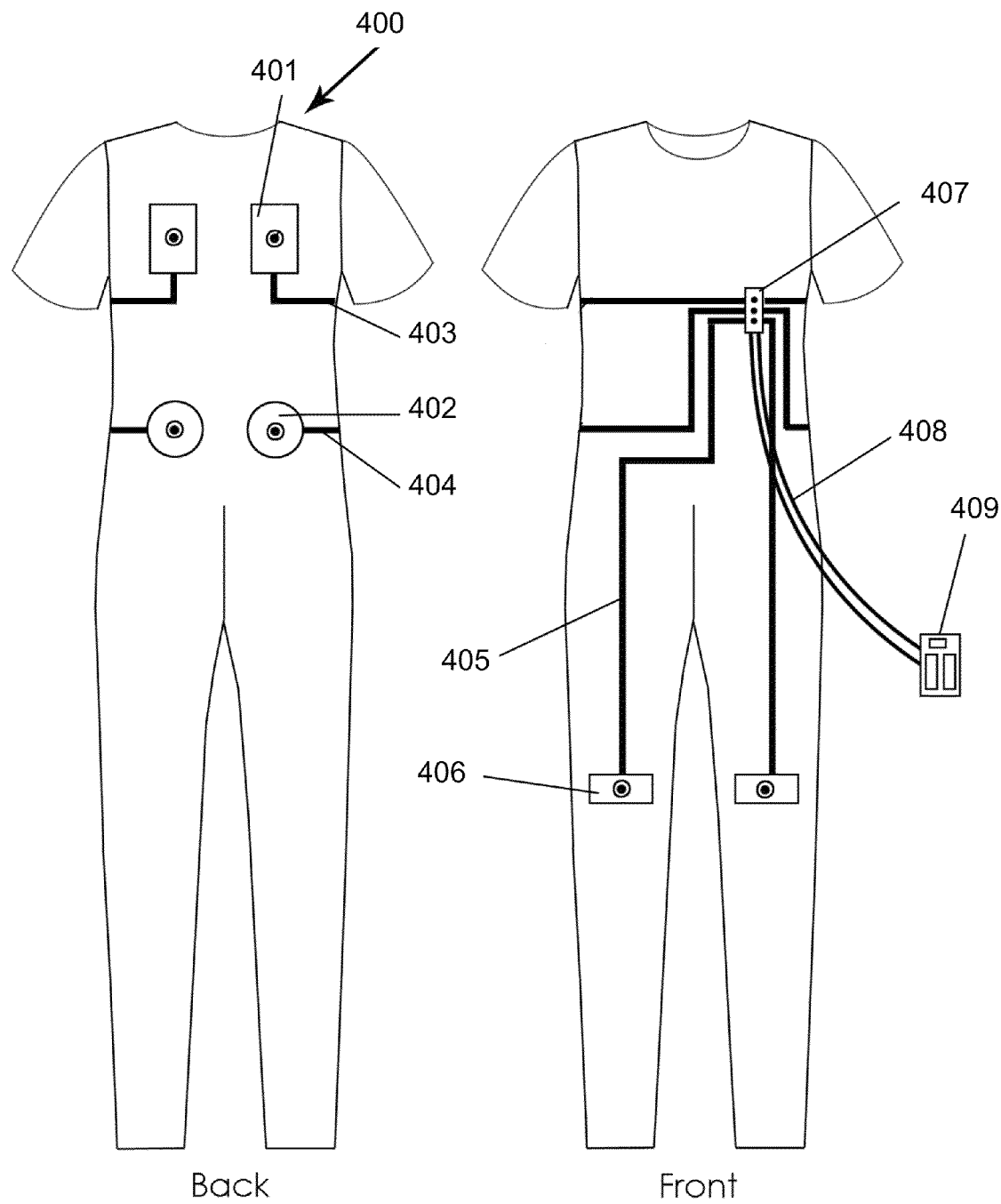
FIGS. 4A and 4B illustrate a back and front view of a full-body garment according to another embodiment of the present invention.

FIGS. 4A and 4B illustrates a back and front view of a full-body garment 400, respectively, in accordance with another embodiment of the present invention. Electrodes 401 are connected with conductive path 403 to form a treatment area (i.e., back area); electrodes 402 are connected with conductive path 404 to form a treatment area (i.e., low back area); and electrodes 406 are connected with conductive paths 405 to form a treatment area (i.e., knee area). Conductive paths 403, 404 and 405 are made with conductive textiles materials and are connected with electronic stimulation signal controller 409 via electrical cables 408. As shown in FIG. 4, the garment may include control switch 407 for switching the conductive paths, and thus, activating the selected group of electrodes connected with the corresponding conductive path. In this regard, the present invention allows a user to use the electronic stimulation garment while the electronic stimulation signal controller 409 connects with garment, also, the electronic stimulation signal controller can be detached from the garment. Furthermore, the electrode 401, 402 and 406 can be designed with different shapes and sizes.

The electrodes as shown in FIGS. 4A and 4B are the same as the electrodes described above in connection with FIGS. 1A and 1B. Thus, the descriptions thereof are omitted.

The electronic stimulation signal controller may contain at least two output terminals. A positive output terminal and a negative output terminal. Each terminal can be connected to the conductive path. The number of the textile electrode pairs is not limited to any specific number in which the clothing prototype was designed, and depends on the size of electrodes and conductive paths in the fabric.

Figure 5A:
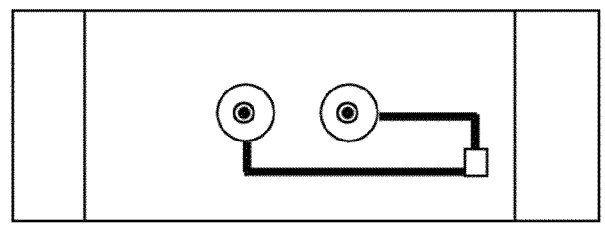
FIGS. 5A to 5D illustrate other textile accessories according to another embodiment of the present invention.
Figure 5B:
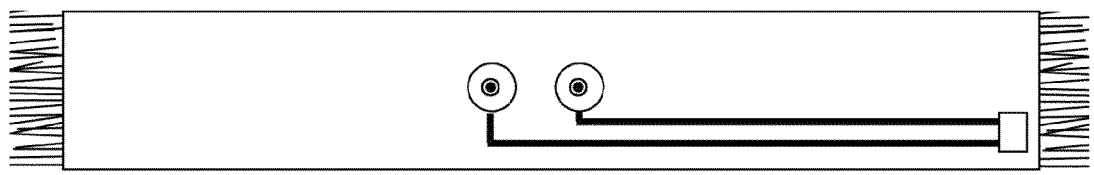
Figure 5C:
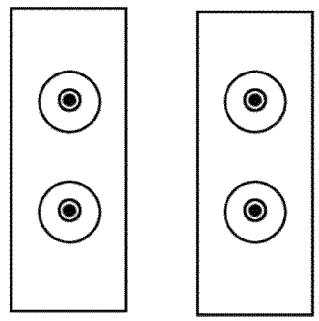
Figure 5D:
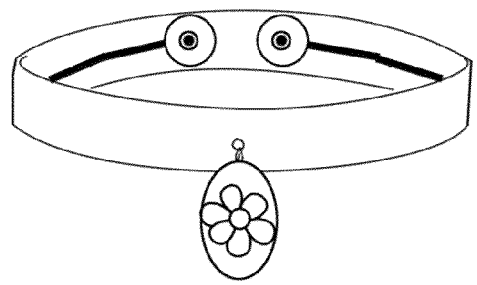

FIGS. 5A to 5D illustrate the electronic stimulation textiles accessories, such as belt (FIG. 5A), scarf (FIG. 5B), kneecaps (FIG. 5C), and necklace (FIG. 5D). The electrodes as shown in FIGS. 5A to 5D are the same as the electrodes described above in connection with FIGS. 1A and 1B. Thus, the descriptions thereof are omitted.

The garments shown in FIGS. 5A to 5D can also provide electronic stimulation therapy as described above. Similarly, the invention may also be applied to other textiles products such as t-shirt, underwear, sportswear, sweater, knitwear, trousers, footwear, wrist/finger band support, ankle/foot band support, localized elbow/knee support band, home products, medical products and the like.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

What is claimed is:
1. A textile for providing traditional Chinese medicine therapy to a wearer using electronic stimulation, comprising:
  two conductive areas that are made from conductive textile material, the conductive areas are separated by nonconductive textile material, wherein the conductive areas are not enclosed within the nonconductive textile material;

a plurality of metallic connectors directly arranged in a two dimensional array on each of the two conductive areas, the connectors are connected with a plurality of textile electrodes corresponding to specific acupoints of a wearer; and an electronic stimulation signal controller configured to conduct electronic stimulation signals to the textile electrodes via the metallic connectors, wherein each of the textile electrode includes a liquid absorbent layer and an electricity conductive layer, and each of the textile electrode is detachable from the textile via the metallic connectors.

2. The textile according to claim 1, further comprises a switch unit configured to activate a subset of the textile electrodes.

3. The textile according to claim 1, wherein the metallic connectors are metallic buttons.

4. The textile according to claim 1, wherein the conductive textile material and the nonconductive textile material are connected together by textile technologies.

5. The textile according to claim 4, wherein the textile technologies include knitting, weaving, attaching, embroidering, sewing and printing.

6. The textile according to claim 1, wherein the conductive material is capable of conducting electricity.

7. The textile according to claim 1, wherein the electronic stimulation is Transcutaneous Electrical Nerve Stimulation.

8. The textile according to claim 1, wherein the electronic stimulation signal controller is controlled either by an embedded system, a wired device, or a remote device wirelessly.

9. The textile according to claim 1, further comprises a power source adapted to supply power to the electronic stimulation signal controller, wherein the power source includes direct current, alternating current, batteries, or renewable power.

10. The textile according to claim 1, wherein the textile is in the form of a textile product.

11. The textile according to claim 10, wherein the textile product is a t-shirt, underwear, sportswear, sweater, or knitwear.

* * * * *